US007972605B2

(12) United States Patent
Patel et al.

(10) Patent No.: US 7,972,605 B2
(45) Date of Patent: Jul. 5, 2011

(54) MODIFIED VACCINIA ANKARA VIRUS VACCINE

(75) Inventors: Dhavalkumar D. Patel, Reinach (CH); David J. Pickup, Durham, NC (US)

(73) Assignee: Duke University, Durham, NC (US)

( * ) Notice: Subject to any disclaimer, the term of this patent is extended or adjusted under 35 U.S.C. 154(b) by 1 day.

(21) Appl. No.: 12/310,781

(22) PCT Filed: Sep. 10, 2007

(86) PCT No.: PCT/US2007/019607

§ 371 (c)(1),
(2), (4) Date: Mar. 6, 2009

(87) PCT Pub. No.: WO2008/076157

PCT Pub. Date: Jun. 26, 2008

(65) Prior Publication Data

US 2009/0274723 A1 Nov. 5, 2009

Related U.S. Application Data

(60) Provisional application No. 60/842,992, filed on Sep. 8, 2006, provisional application No. 60/849,845, filed on Oct. 6, 2006.

(51) Int. Cl.
*A61K 39/285* (2006.01)
*C12N 7/01* (2006.01)
*C12N 15/863* (2006.01)

(52) U.S. Cl. ............... 424/199.1; 424/232.1; 435/235.1; 435/320.1

(58) Field of Classification Search ........................ None
See application file for complete search history.

(56) References Cited

U.S. PATENT DOCUMENTS 6,440,422 B1 8/2002 Sutter et al.
6,682,742 B1 * 1/2004 Wintersperger et al. ... 424/199.1

FOREIGN PATENT DOCUMENTS

WO WO 03/097844 * 12/2003

OTHER PUBLICATIONS

McKelvey et al (Journal of Virology 76:11216-11225, 2002).*
Antoine et al, Virology 244:365-396, 1998.*
International Search Report for PCT/US2007/019607 mailed Jul. 28, 2008.
Written Opinion for PCT/US2007/019607 mailed Jul. 28, 2008.
McKelvey et al., "Identification of the Orthopoxvirus p4c Gene, Which Encodes a Structural Protein That Directs Intracellular Mature Virus Particles into A-Type inclusions", *Journal of Virology*, Nov. 2002, vol. 75, No. 22, pp. 11216-11225.
Boulanger et al., "Identification and Characterization of Three Immunodominant Structural Proteins of Fowlpox Virus", *Journal of Virology*, Oct. 2002, vol. 76, No. 19, pp. 9844-9855.
Ulaeto et al, "The Vaccinia Virus 4c and A-Type Inclusion Proteins Are Specific Markers for the Intracellular Mature Virus Particle", Journal of Virology 70(6):3372-3377 (1996).
Ichihashi, Y., "Unit Complex of Vaccinia Polypeptides Linked by Disulfide Bridges", Virology 113:277-284 (1981).
Antoine et al, "The Complete Genomic Sequence of the Modified Vaccinia Ankara Strain: Comparison with Other Orthopoxviruses", Virology 244:365-396 (1998).
Howard et al, "Vaccinia Virus A26 and A27 Proteins Form a Stable Complex Tethered to Mature Virions by Association with the A17 Transmembrane Protein", Journal of Virology 82(24):12384-12391 (2008).
Howard et al, "Congregation of Orthopoxvirus Virions in Cytoplasmic A-Type Inclusions is Mediated by Interactions of a Bridging Protein (A26p) with a Matrix Protein (ATIp) and a Virion Membrane-Associated Protein (A27p)", JVI Accepts, published online ahead of print on May 19, 2010.
Ifeanyi Okeke et al, "Comparative sequence analysis of A-type inclusion (ATI) and P4c proteins of orthopoxviruses that produce typical and atypical ATI phenotypes", Virus Genes, published online: Jun. 16, 2009.
Meisinger-Henschel et al, "Introduction of the Six Major Genomic Deletions of Modified Vaccinia Virus Ankara (MVA) into the Parental Vaccinia Virus Is Not Sufficient to Reproduce an MVA-Like Phenotype in Cell Culture and in Mice", Journal of Virology 84(19):9907-9919 (2010).
Vaccinia virus P4c (p4c) gene, complete cds, GenBank: AF464893.2, Accession No. AF464893, Version AF464893.2 GI:311977070.

* cited by examiner

*Primary Examiner* — Mary E Mosher
(74) *Attorney, Agent, or Firm* — Nixon & Vanderhye

(57) ABSTRACT

The present invention relates, in general, to vaccines and, in particular, to a modified vaccinia Ankara (MVA) virus, to a composition comprising such a virus and to methods of using same to induce an immune response.

24 Claims, 4 Drawing Sheets

Figure 1A                Figure 1B

Insertion of the VV *p4c* gene into the genome of CPXV BR is sufficient to convert the phenotype of the ATIs from V⁻ (lacking IMV) to V⁺ (containing IMV). Human 143B cells were infected with 10 PFU/cell of CPXV. 18 hr after infection, the cells were fixed, stained, sectioned, and examined by electron microscopy. The panels show sections of cells infected with: (A) CPXV BR (p4c1, ati), which produces V− ATIs; and (B) CPXV A505 (p4c1, p4c, ati), which is a recombinant CPXV containing the VV WR p4c gene under the control of its own promoter. ATIs in cells infected with CPXV A505 have a V+ phenotype. The scale bars each represent 1000 nm.

An electron micrograph of a V+ ATI attached to the surface of a 293 cell.

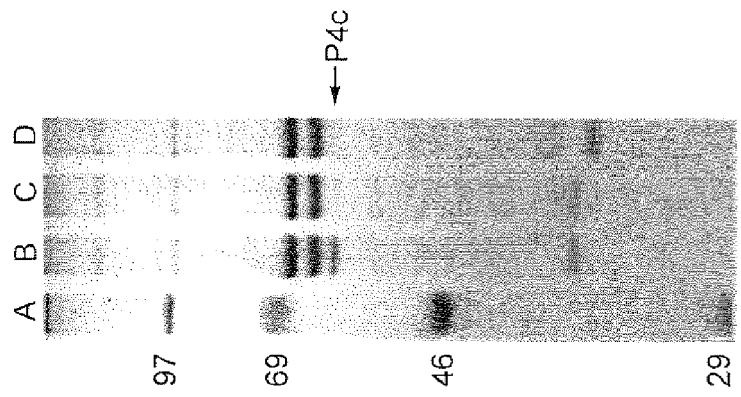

Figure 4

The P4c protein is one of the most abundant structural proteins. Here in lane B the P4c protein is visualized by coomassie blue staining; the two slightly larger proteins are the 4a and 4b proteins. Lanes contain proteins of purified: VV-WR (lane A); a p4c gene deletion variant of VV-WR (lane C) and cowpox virus BR lacking p4c gene(lane D).

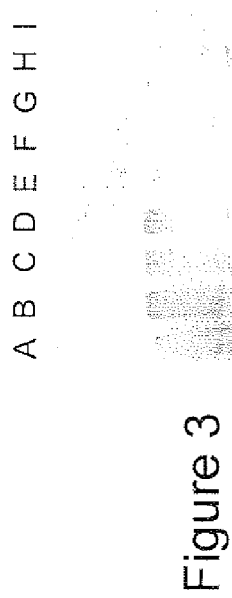

Figure 3

The 94 kDa Ati protein encoded by vaccinia virus (WR) is abundant enough to be visualized by coomassie blue staining of proteins of infected cells (lane I, uninfected cells; lanes A-H, infected cells at 1,3.5,8,11,15,20, and 24 hr post-infection).

VV-WR expressing the *p4c* gene can provide a factor needed to direct the inclusion of IMV within ATIs. Human 143B cells were infected with 10 PFU of one strain of poxvirus/cell (A and C) or with 5 PFU each of two strains of poxvirus/cell (B and D). Eighteen hours after the cells were infected, they were fixed, stained, sectioned, and examined by electron microscopy to identify the phenotype of the ATIs present in the infected cells. Shown are sections of cells infected with VV-WR (*p4c ati1*) (A); VV-WR and CPV-BR (*p4c1 ati*), where the large mass is a $V^+$ ATI (B); vaccinia virus Copenhagen [ $\Phi(p4c^-\Delta ati)$] (C); and vaccinia virus Copenhagen and CPV-BR, where the large mass is a $V^-$ ATI (D). Bars, 1,000 nm.

MODIFIED VACCINIA ANKARA VIRUS VACCINE

This application is the U.S. national phase of International Application No. PCT/US2007/019607 filed 10 Sep. 2007 which designated the U.S. and claims priority to U.S. Provisional Application No. 60/842,992 filed 8 Sep. 2006 and 60/849,845 filed 6 Oct. 2006, the entire contents of each of which are hereby incorporated by reference.

The present invention was made with government support under Grant Nos. 1 U54 AI 057157 and AI 32982 awarded by the National Institutes of Health. The government has certain rights in this invention.

TECHNICAL FIELD

The present invention relates, in general, to vaccines (e.g., poxvirus vaccines and vaccinia virus vaccines) and, in particular, to a modified vaccinia ankara (MVA) virus, to compositions and kits comprising such a virus or viruses and to methods of using same to induce an immune response.

BACKGROUND

The current MVA virus vaccine provides an extremely safe alternative to the currently available smallpox vaccines that are associated with a significant degree of adverse effects. However, replication of MVA virus is impaired in human cells and cells of many animal species, providing a natural limitation on infections with this virus. Thus, large doses of MVA are needed, and multiple doses are required for effective protection against smallpox and other agents. Methods to enhance the immunogenicity of this vaccine virus, preferably to the point of reducing the vaccination to a single dose, would significantly enhance the efficacy of this vector.

One of the unusual features of poxviruses is their ability to produce virus particles of more than one type. The majority of the orthopoxviruses can produce infectious virus particles of several types differing in either surface structure or site of accumulation. Most abundant, and often representing more than 90% of virus progeny, are the intracellular mature viruses (IMVs), which are generally thought to possess a single membrane. A small proportion of the IMV are converted to intracellular enveloped virus (IEVs), which are IMV wrapped in double membranes derived from the trans-Golgi network or tubular endosomes. The IEV are transported to the cell surface, where their outer membranes fuse with the plasma membrane to produce either the released, extracellular enveloped virus (EEV) or the cell-associated enveloped virus (CEV), which remains attached to the cell surface. Those IMVs that are not converted into IEV, CEV, or EEV, remain in the cytoplasm of the cell, either as free particles, or as particles embedded within A-type inclusions (ATIs). ATIs are large, well-defined proteinaceous bodies produced in cells infected with certain strains of cowpox, ectromelia, raccoonpox virus, fowlpox virus, or canarypox viruses (FIG. 1). The different kinds of virus particles have distinct physical, immunological, and biological properties, suggesting that particles of each type provide some advantages for virus replication, however, the in vivo roles of particles of each of these types are not fully understood.

The inclusion of IMV within the ATIs is determined by two factors, the synthesis of an ATI matrix protein, and the synthesis of the P4c protein, which directs the IMV into the ATIs (FIG. 1). Both the ati gene (Patel and Pickup, EMBO J. 6(12):3787-3794 (1987), Patel et al, Virology 149(2):174-89 (1986)), and the p4c gene (McKelvey et al, J. Virol. 76(22): 11216-25 (2002)) have been identified. Interestingly, although few orthopoxviruses synthesize ATIs (because they encode truncated ATI proteins), most orthopoxviruses, including variola and monkeypox viruses, encode a P4c protein. Consequently, in orthopoxviruses of most types, including variola virus, the repair of a single gene, the ati gene, or the provision of the ATI protein by complementation, will result in the production of ATIs containing IMV.

Presumably, the virus-containing ATIs ($V^+$ ATIs) facilitate the transmission of the virus particles from one host to another. The role of the ATI in virus dissemination and pathogenesis within the infected animal is unknown. The effects of ATIs upon immunity to the virus are also unknown. The IMVs within an ATI are expected to be inaccessible to antibodies that might otherwise neutralize these particles. Moreover, the properties of the ATIs suggest that the IMV within ATI particles are likely to be resistant to antibody neutralization of virus infectivity, whatever the nature of the antibodies (anti-IMV, EEV or ATI).

Currently, it is unclear how IMVs within ATIs might become able to infect host cells. Initial analyses of the fate of $V^+$ATIs added to human 293 cells (FIG. 2) suggest that the ATIs can adhere to target cells, and then IMVs at the interface between the cell and the ATI are able to initiate an infection through the plasma membrane. Cell surface proteases may facilitate the degradation of ATI protein to release the IMV, while maintaining the IMV in a protected environment between the ATI and the cell surface. In this way, the ATI will release only a portion of its IMVs to infect one cell, while retaining the remainder to infect other cells. In effect, the ATI could act as a delivery vehicle to inoculate multiple IMVs into a number of different cells over a period of time, and at the same time protect the embedded IMVs from physical and immunological inactivation. This type of infection process might well protect the IMVs from complement-mediated attack or any neutralizing antibodies that might otherwise interfere with the process of IMV infection.

In addition to affecting the uptake of infectious virus, the two proteins required for $V^+$ ATI formation are likely to be important targets for immune responses. The ATI protein is typically one of the most abundant proteins synthesized in orthopoxvirus infected cells, even if the virus, like vaccinia virus (FIG. 3) encodes a truncated protein (the 94 kDa ATI protein) incapable of forming discrete ATIs. The P4c protein is highly conserved among orthopoxviruses, including variola virus, and it is the largest IMV surface protein, and one of the most abundant IMV surface proteins (Katz and Moss Proc. Natl. Acad. Sci. USA 66(3):677-84 (1970), Katz and Moss, J. Virol. 6(6):717-26 (1970), Sarov and Joklik, Virology 50(2):579-92 (1972)) (FIG. 4). Two early studies (Oie and Ichihashi, Virology 157(2):449-59 (1987), Stern and Dales, Virology 75(1):232-41 (1976)) suggested that the P4c protein is a target for antibodies capable of neutralizing IMV, although Dales later reported an inability to confirm this (Wilton et al, Virology 214(2):503-11 (1995)).

The present invention relates to MVA virus vaccine modified by repair of two inactivated viral genes to forms that embed the infectious virus in ATI particles. These vaccines have greater utility and efficacy than current MVA vaccine viruses because of enhanced particle stability, enhanced deliverability by nasal, dermal, intramuscular or oral routes, reduced release of infectious virus and enhanced immunogenicity.

SUMMARY OF THE INVENTION

The present invention relates generally to vaccines. Specifically, the invention relates to an MVA virus, to compositions and kits comprising the virus and to methods of using same.

Objects and advantages of the present invention will be clear from the description that follows.

BRIEF DESCRIPTION OF THE DRAWINGS

FIGS. 1A and 1B. Insertion of the VV p4c gene into the genome of CPXV BR is sufficient to convert the phenotype of the ATIs from V⁻ (lacking IMV) to V⁺ (containing IMV). Human 143B cells were infected with 10 PFU/cell of CPXV. 18 hr after infection, the cells were fixed, stained, sectioned, and examined by electron microscopy. The panels show sections of cells infected with: (FIG. 1A) CPXV BR (p4c1, ati), which produces V– ATIs; and (FIG. 1B) CPXV A505 (p4c1, p4c, ati), which is a recombinant CPXV containing the VV WR p4c gene under the control of its own promoter. ATIs in cells infected with CPXV A505 have a V+ phenotype. The scale bars each represent 1000 nm. (McKelvey et al, J. Virol. 76(22):11216-25 (2002)).

FIG. 3. The 94 kDa Ati protein encoded by vaccinia virus (WR) is abundant enough to be visualized by coomassie blue staining of proteins of infected cells (lane I, uninfected cells; lanes A-H, infected cells at 1,3,5,8,11,15,20, and 24 hr post-infection). (Patel et al, Virology 149(2):174-89 (1986)).

FIG. 4. The P4c protein is one of the most abundant structural proteins. Here in lane B, the P4c protein is visualized by coomassie blue staining; the two slightly larger proteins are the 4a and 4b proteins. Lanes contain proteins of purified: VV-WR (lane A); a p4c gene deletion variant of VV-WR (lane C) and cowpox virus BR lacking p4c gene (lane D). (McKelvey et al, J. Virol. 76(22):11216-25 (2002)).

FIGS. 5A-5D. VV-WR expressing the p4c gene can provide a factor needed to direct the inclusion of IMV within ATIs. As described by McKelvey et al (J. Virol. 76:11216-25 (2002)), human 143B cells were infected with 10 PFU of one strain of poxvirus/cell (FIGS. 5A and 5C) or with 5 PFU each of two strains of poxvirus/cell (FIGS. 5B and 5D). Eighteen hours after the cells were infected, they were fixed, stained, sectioned, and examined by electron microscopy to identify the phenotype of the ATIs present in the infected cells. Shown are sections of cells infected with VV-WR (p4c ati1) (FIG. 5A); VV-WR and CPV-BR (p4c1 ati), where the large mass is a V⁺ ATI (FIG. 5B); vaccinia virus Copenhagen [Φ(p4c'-Δati)] (FIG. 5C); and vaccinia virus Copenhagen and CPV-BR, where the large mass is a V⁻ ATI (FIG. 5D). Bars, 1,000 nm.

DETAILED DESCRIPTION OF THE INVENTION

Figure 2:
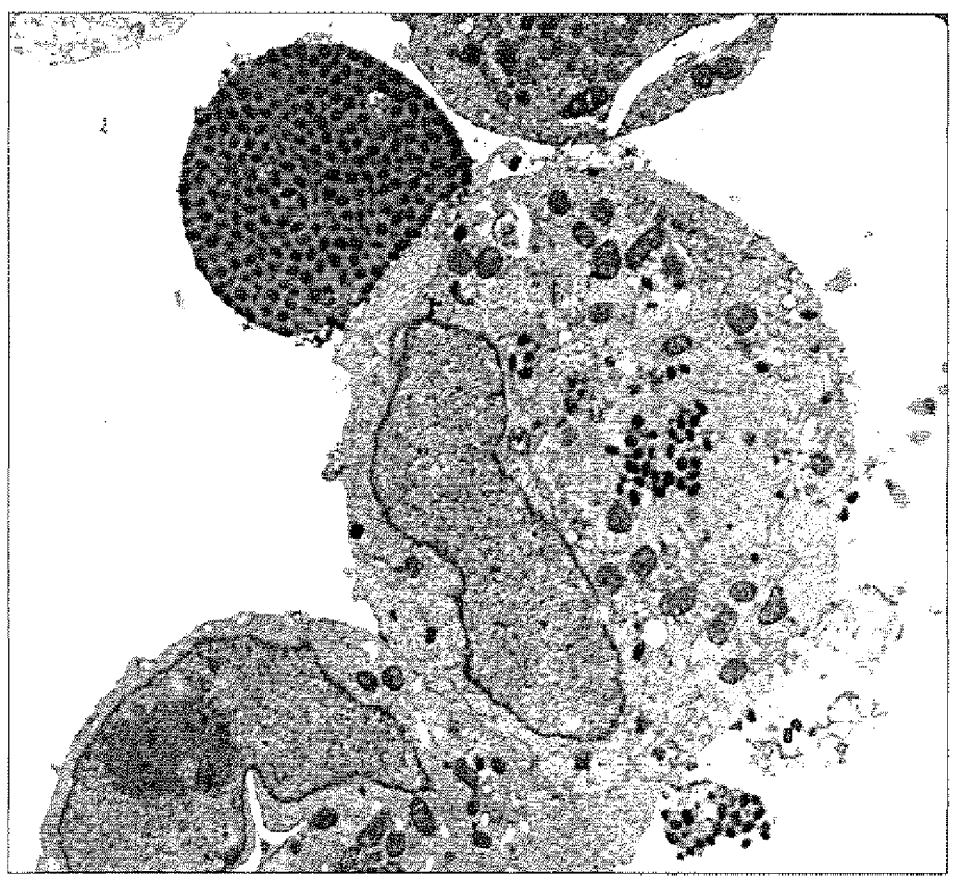
FIG. 2. An electron micrograph of a V+ ATI attached to the surface of a 293 cell.

In the context of vaccinia virus vaccines, the vaccinia virus MVA lacks intact copies of the two genes (the ati gene and the p4c gene) required to generate the ATIs containing IMV. The present invention results, at least in part, from the realization that repair of these two genes, or provision of the products of these two genes (either by genetic recombination or complementation), can provide a vaccinia virus that embeds IMVs within the ATIs (MVA-ATI). MVA virus vaccines so modified are superior to current MVA vaccine viruses because of the following:

(i) extended time of release of infectious virus from the ATIs after inoculation resulting in multiple reimmunizations from a single dose of vaccine virus;

(ii) greater immunogenicity against virulent orthopoxviruses because the MVA-ATI expresses both the ATI protein, the most abundant orthopoxvirus protein, and the P4c protein, the largest and one of the most abundant virion surface proteins (P4c is reported to be a target of neutralizing antibodies);

(iii) enhanced ability of virus delivery by nasal, intradermal, intramuscular or oral routes;

(iv) enhanced particle stability, which can contribute both to vaccine stability in the field (and reduce or eliminate the need for refrigeration when hydrated), and the ease of purification of the virus vaccine, and (v) the ATI protein can provide a matrix that facilitates attachment of the embedded infectious virus onto solid microneedles (in the form of patches) that can be used for intradermal delivery of the virus. The ATI protein can allow stabilization/maintenance of infectivity of virus inocula adhered to the microneedles, as per description in (iv). (Wang et al, J. Invest. Dermatol. 126:1080-1087 (2006), Mikszta et al, J. Infect. Dis. 191:278-88 (2005), McAllister et al, Proc. Natl. Acad. Sci. 100:13755-13760 (2003).).

The present invention relates to MVA vaccines with improved efficacy against variola virus and related virulent poxviruses. Expression of ATI and P4c is not expected to increase the capacity of MVA to replicate in human or mouse cells. Thus, the pathogenic and host range properties of the MVA vaccine of the invention are not likely to be adversely affected by expression of these two proteins.

An MVA recombinant virus (MVA-ATI) of the invention that expresses the vaccinia virus P4c and cowpox virus ATI proteins can be prepared using standard techniques (see Example 1). Briefly, and by way of example, an insertion plasmid DNA can be prepared that contains a region spanning the 3' end of the rpo132 gene, the cowpox virus ati gene, the vaccinia virus p4c gene, and the 3' end of the A27L (14K) gene, in the same way that these genes are arranged in the orthopoxvirus genome. In addition, a selectable marker gene can be included in the intergenic region between, for example, the p4c gene the A27L gene. Recombinant MVA possessing the insertion of this fragment (with the marker gene) can be selected during culture of the progeny virus from cells that have been infected with unmodified MVA and transfected with insertion plasmid DNA. The insertion plasmid DNA can have been cut at sites in or near the ends of the rpo132 gene, and the A27L gene to facilitate recombination in these two gene, which flank the ati and p4c genes. A double-crossover event at these two sites results in the substitution of the disrupted ati and p4c genes of MVA with the full-length functional versions of these genes present in the DNA of the insertion plasmid. Clonal isolates of recombinant virus selected in this way can then be obtained through successive rounds of plaque purification. The genetic purity of the recombinant MVA can be determined by PCR and DNA hybridization methods. The expression of the P4c and Ati proteins by the recombinant MVA viruses can be confirmed by protein analyses of both purified virus/ATI preparations and lysates of virus-infected cells. The production of ATIs can be assessed by light microscopy and immunohistochemistry. The production of V⁺ ATIs can be assessed by electron microscopy.

Alternatively, a binary virus vaccine system can be employed as described in the Examples that follow (note, particularly, Example 3).

V⁺ ATIs can be isolated using, for example, a procedure modified from that described by Patel et al (Virology 149(2): 174-89 (1986)). (See Example 5.)

MVA-ATI can be used as a medical or veterinary vaccine platform for use in vaccine recipients that already possess some degree of immunity to either poxviruses (through infection with one or more poxviruses, or by previous vaccination with poxviruses or vaccines designed to protect against poxviruses), or the immunogens encoded by the MVA-ATI vector. Current vaccines (particularly protein sub-unit vaccines, DNA vaccines, live, attenuated-virus vaccines, and replication-deficient virus vaccines, as well as many replication-competent, live-virus vaccines) often require more than one immunization to induce protective levels immunity. However, administration of booster immunizations with the same virus vector as that employed in the primary immunization can be problematic. Immune responses resulting from the primary immunization that targeted the virus vector may suppress the replication and gene expression of the virus in the booster immunization to the point of abrogating enhancement of immunity against the target protein by the booster dose of virus.

In accordance with the present invention, the ATI-matrix protein can protect embedded virus particles from neutralizing antibodies and complement-mediated inactivation. This enables the embedded particles to initiate infections even in humans and non-human animals with existing immune responses against virus contained within the ATIs. Thus, in populations that have some immunological responses to poxvirus vaccines (e.g., patients previously immunized with vaccinia virus vaccines), an MVA-ATI vaccine can provide an effective booster of the immunity against vaccinia virus previously acquired. An MVA-ATI vaccine can also provide an effective way to boost immunity to immunogens delivered in previous vaccines (either poxvirus vector vaccines or alternative non-homologous vaccines). In addition, an MVA-ATI vaccine can be used to deliver new immunogens to recipients of previous vaccinia virus vaccines.

One use of a vaccinia virus vaccine is to rapidly induce protective immunity (or boost pre-existing immunity) in the period following a patient's exposure and infection with variola virus. While data on the efficacy of vaccination with vaccinia virus vaccines at various periods after infection with variola virus are limited, there can be beneficial effects, particularly, when the post-exposure vaccine is administered within a few days of infections, and where the infected individual has some pre-existing immunity towards variola virus. In these circumstances, and for the reasons noted above, the MVA-ATI vaccine can be superior to other vaccinia virus vaccines in establishing an infection that provides protection. The MVA-ATI vaccine can be less susceptible to neutralization by immune responses resulting either from previous vaccinations or from cross-neutralizing antibodies generated by the variola virus infection.

In addition to the use of ATIs to deliver virus for vaccine purposes, ATIs can also be used to deliver poxviruses that specifically replicate in tumor cells. Recently, the use of viruses to kill tumor cells in vivo has become a focus of much research (Shen et al, Mol. Ther. 11:180 (2005); Wang et al, Proc. Natl. Acad. Sci. USA 103:4640 (2006)). In the poxvirus family, both vaccinia virus and myxoma virus have been used as viral oncolytic agents. Many to the features of the ATI that can be useful in the context of vaccines, can also be useful in the in vivo delivery of oncolytic poxviruses. ATI-poxvirus oncolytic agents can be produced via the addition of p4c and Ati genes to a poxvirus (including myxoma and vaccinia viruses).

The ATI matrix provides a malleable, particulate matter, which, through milling, size selection, or other processing, provides a way to control the size and surface properties of the V+plus ATIs to optimize their properties for:
 i) airborne transmission;
 ii) delivery into the lung (distribution of particles within the lung is highly dependent upon the size of the particle);
 iii) delivery by the oral route;
 iv) timing of infection after particle uptake (for example, by increasing the ratio of ATI matrix to virus particles, the time taken for proteolytic degradation of ATI to release infectious virus can be increased);
 v) uptake by phagocytosis (which can be influenced by particle size);
 vi) uptake by cells of specific types (e.g., only proteases secreted from cells of certain types may be capable of degrading the ATIs to liberate infectious virus);
 vii) protecting embedded virus from inactivation by ultraviolet light, heat inactivation, dessication, solvents that can destroy the viral membrane (and infectivity), proteases that damage the viral surface proteins, and other agents typically used to inactivate infectious agents (perhaps permitting the formulation of vaccines that do not require refrigeration and/or lyophilization); and
 viii) targeting of specific cells by inclusion of proteins or other moieties promoting the specific association between the ATIs (containing viruses) and target cells, thereby providing specificity at the level of the ATI protein wrapping the infectious virus, in addition to any specificity imparted by the virus particles themselves (this type of targeting can be useful for targeting of virus to tumor cells, or targeting of virus to particular immune cells that promote immune responses, or targeting of virus vectors involved in gene therapy).

The ATI matrix also provides a stabilizing wrapper around the virus particles, providing a means for both stabilizing the virus and facilitating the purification of the embedded virus (through the sedimentation and density properties of the ATIs or through affinity chromatography procedures designed to purify the Ati protein or moieties attached to or fused with the Ati protein).

While the embodiments detailed above are described with reference to MVA, ATIs can be used similarly with any of the orthopoxviruses and the majority of poxviruses.

The present invention relates to the MVA-ATI virus vaccine and also to compositions, e.g., pharmaceutical compositions, comprising the MVA-ATI virus that are suitable for use in inducing an immune response in a living animal body, including a human. The pharmaceutical composition can include one or more pharmaceutically acceptable and/or approved carriers, additives, antibiotics, preservatives, adjuvants, diluents and/or stabilizers. Such auxiliary substances can be water, saline, glycerol, ethanol, wetting or emulsifying agents, pH buffering substances, or the like. Suitable carriers include, but are not limited to, slowly metabolized molecules such as proteins, polysaccharides, polylactic acids, polyglycolic acids, polymeric amino acids, amino acid copolymers, lipid aggregates, or the like. The composition can be formulated, for example, for administration by injection. Alternatively, the composition can be formulated so as to be suitable for nasal or oral administration. The composition, advantageously sterile, can be present in dosage unit form.

The present invention also relates to kits comprising the MVA-ATI virus disposed within a container means. The kit can include solvents (e.g., buffers) and/or other agents to be administered with the virus, including, but not limited to, adjuvants.

Certain aspects of the invention are described in greater detail in the non-limiting Examples that follow (see also McCurdy et al, Clin. Infect. Dis. 38:1749 (2004)).

EXAMPLE 1

Standard methods can be used to generate two recombinant vaccinia MVA viruses. To identify recombinant viruses, insertion cassettes can be used that contain a marker gene, *E.* coli gpt gene encoding xanthine-guanine phosphoribosyltransferase under the control of an early/late promoter (short synthetic promoters with different sequences can be used to minimize the possibility of recombination between the inserted promoter elements and authentic promoter elements in the MVA genome). MVA viruses containing the inserted gpt gene can be identified by selecting foci of virus-infected cells as described (Falkner and Moss, J. Virol. 62(6):1849-54 (1998)). MVA seldom forms easily recognizable plaques in BHK cells, although infected cells are frequently identifiable because of altered morphology. To help visualize infected cells without insertion of another marker into the virus genome, plasmids containing either the green fluorescent protein (GFP) gene or E. coli beta-glucuronidase (GUS) gene, each under transcription control of a vaccinia virus early/late promoter, can be transfected into monolayers of cells used for plaque selection. Identification of cells containing MVA viruses directing transcription of the plasmid GUS gene can be effected by selecting foci of virus-infected cells producing a blue color in the presence of X-Gluc (Carroll et al, Biotechniques 19(3):352-4, 356 (1995)). Alternatively, cells containing MVA viruses directing transcription of the plasmid GFP gene can be identified by selecting foci of virus-infected cells producing a green color upon excitation by ultraviolet light. The transient expression after transfection (Cochran et al, Proc. Natl. Acad. Sci. USA 82(1):19-23 (1985)) can be of assistance in identification and then extraction of virus from isolated plaques. However, if the efficiency of this assay is too low, either the GUS or GFP gene can be inserted into the MVA genome to permit identification of each infected cell. After further passage, PCR amplification (Staib et al, Methods Mol. Biol. 269:77-100 (2004)) and DNA sequence analyses can be used on virus DNA isolated from cells infected with recombinants to confirm the substitution of the targeted gene. To allow quantification of viral gene expression in harvested mouse tissues (which may not support the production of infectious virus that can be measured by plaque assay), and to determine the extent of viral dissemination within the mouse, a functional luciferase gene can be inserted into the MVA genome, as described (Ramirez et al, Arch. Virol. 148(5):827-39 (2003)).

The MVA-ATI virus can be constructed, for example, to express the functional ati gene from cowpox virus and a functional p4c gene from vaccinia virus WR (McKelvey et al, J. Virol. 76(22):11216-25 (2002)), as well as the luciferase gene. In the MVA virus genome, the remnants of the adjacent ati and p4c genes are present, but neither full-length Ati nor full-length P4c proteins are produced (Antoine et al, Virology 244(2):365-96 (1998)). Therefore, for the control MVA virus, a two-gene luciferase-gpt cassette can be inserted into the genome immediately downstream of the A27L gene, immediately upstream of the truncated p4c gene (Antoine et al, Virology 244(2):365-96 (1998), Patel and Pickup, EMBO J. 6(12):3787-3794 (1987), Patel and Pickup, J. Virol. 63(3):1076-86 (1989)). These genes can be inserted to effect transcription in the same orientation as that of the p4c gene and thereby reduce the potential for transcriptional interference from the inserted cassette. This position is within the central conserved region of the virus genomes, where it is expected to be more stable than in the terminal regions of the viral genome that are subject to spontaneous transposition and deletion events (Archard and Mackett, J. Gen. Virol. 45(1):51-63 (1979), McFadden and Dales, Cell 18(1):101-8 (1979), Moyer et al, Cell 22(2 Pt 2):545-53 (1980), Pickup et al, Proc. Natl. Acad. Sci. USA 81(21):6817-21 (1984)). Insertion of these genes into an intergenic region upstream of a locus that appears to be non-functional in this MVA is expected to avoid adverse effects on virus replication. Sequences of the genes within the recombinant viruses, and the in vitro growth properties of recombinant viruses expressing this gene, can be examined to confirm that virus replication is not affected and that gene products are expressed as designed. The MVA control virus (MVAlucgpt) can be identical to the instant MVA vaccine (including possession of the non-functional versions of the P4c and ati genes) except for the expression of the luciferase and gpt genes. The MVA-ATI virus can be similarly constructed except that the insertion cassette can contain the luciferase, gpt, ati and p4c genes, with the latter two functional genes replacing the disrupted ati and p4c genes present in the MVA genome.

The expression of the ATI and P4c proteins by the MVA-ATI recombinant can be confirmed by PAGE analyses of proteins of infected cells (coomassie blue-staining to show the ATI protein, pulse labeling to show both P4c and ATI proteins, and western blot analyses with rabbit anti ATI sera or mouse anti P4c sera). Transmission EM of sections of virus-infected cells can be used to confirm that the MVA-ATI virus produces ATIs containing IMVs.

EXAMPLE 2

Standard methods can be used to generate two recombinant vaccinia MVA viruses. To identify recombinant viruses, insertion cassettes can be used that contain a selectable marker gene, the vaccinia virus K1L gene under the control of its early promoter. MVA viruses containing the inserted K1L gene can be identified by selecting foci of virus-infected cells on rabbit kidney 13 (RK-13) cells, which are non-permissive for MVA virus replication unless a host-range gene such as the K1L gene (Carroll and Moss, Virology 238:198-211 (1997), Meyer et al, J. Gen. Virol. 72 (Pt 5):1031-8 (1991), Ramsey-Ewing and Moss, Virology 222:75-86 (1996), Sutter et al, J. Virol. 68:4109-16 (1994), Wyatt et al, Virology 251:334-42 (1998)) is expressed. To help visualize infected cells, the GFP gene can be inserted into the MVA genome to permit identification of each infected cell. A cassette containing the K1L gene, and also the GFP gene under the control of an early/late promoter, can first be inserted into the genome of the MVA virus using the transient dominant selection method (Falkner and Moss, J. Virol. 64:3108-11 (1990), Staib et al, Biotechniques 28:1137-42, 1144-6, 1148 (2000), Staib et al, Biotechniques 34:694-6, 698, 700 (2003), Tscharke and Smith, Biotechniques 33:186-8 (2002)) to replace the majority of the residual sequences of the inactive K1L gene. By spontaneous recombination between homologous sequences flanking the K1L/GFP gene cassette, an MVA deletion variant (A675) that has lost both the majority of the endogenous disrupted K1L gene, and the entire K1L/GFP gene cassette, can be constructed. The K1L/GFP gene cassette can subsequently be used again as transient dominant selectable marker to insert other genes into the genome of MVA virus A675 with minimal chance of untargeted insertion of the insertion plasmid into the original (now deleted) K1L gene instead of the targeted site. Further, because the genome-integrated cassette is designed to be unstable, this provides us a method of producing recombinant viruses that lack extraneous sequences other than the deliberately inserted sequences. Removal of the selection cassette makes it possible to use the same cassette for sequential manipulations of the viral genome. In addition, it may be important to remove the K1L gene from the recombinant vaccine because the extension of virus host-range may have the undesirable effect of increasing the pathogenicity of this vaccine virus in humans.

The MVA-AT1-2 virus can be constructed, for example, to express the functional ati gene from cowpox virus and a functional p4c gene from vaccinia virus WR (McKelvey et al, J. Virol. 76(22):11216-25 (2002)) by use of an insertion plasmid employing the K1L/GFP gene cassette. Viruses constructed with the K1L gene as a selection marker can be derived from the MVA virus A675 containing the deletion of the remnants of K1L gene present in the unmodified MVA virus genome. In the MVA virus A675 genome, the remnants of the adjacent ati and p4c genes are present but neither full-length Ati nor full-length P4c proteins are produced (Antoine et al Virology 244(2):365-396 (1998). Therefore, to assess the effects of gene insertions into the MVA A675 virus, this virus, rather than the unmodified MVA virus, can be used as a control virus for recombinant derivatives of this virus. The MVA-AT1-2 virus can be similarly constructed (with initial selection for the K1L/GFP gene cassette, and subsequent selection for recombinants that have lost the K1L/GFP gene cassette) except that the residual insertion comprises the ati and p4c genes, with the latter two functional genes replacing the disrupted ati and p4c genes present in the MVA genome.

EXAMPLE 3

A binary virus vaccine can be constructed consisting of V+ MVA recombinant viruses generated as described in Example 2, except that one virus (MVA(delta p4c,ATI)) can express an intact ati gene but not a functional p4c gene, whilst the other virus (MVA(p4c,delta ATI)) can express an intact p4c gene but not a functional ati gene. Thus, neither virus is capable of producing V+ ATIs but coinfection of a cell with these viruses yields V+ATIs by complementation, as described (McKelvey et al, J. Virol. 76:11216-25 (2002)) (see FIG. 5).

The use of this binary system can circumvent problems associated with the plaque purification of recombinant viruses from parental viruses when viruses of all types are embedded together within ATIs. This is useful not only for the isolation of MVA viruses expressing both the ati and p4c genes, but also for derivative MVA vaccine viruses expressing other genes that have to be inserted into the vaccine virus genomes. For example, to create an MVA-ATI vaccine expressing the influenza virus hemagglutinin (HA) gene, the HA gene can be inserted into either or both of the MVA(delta p4c,ATI) and the MVA(p4c,delta ATI) viruses. Coinfection of permissive cells with these two viruses results in the production of V+ ATIs containing viruses of both types. These V+ ATIs provide an inoculum suitable for use in vaccination.

EXAMPLE 4

Studies can be performed to determine if recombinant MVA viruses that form ATIs are superior to unmodified MVA virus in their ability to induce MVA-specific humoral and cell-mediated immune responses. C57BU6 female mice (5 per group; each experiment repeated twice) can be inoculated intranasally (IN), intramuscularly, intragastrically or intradermally (ID) with control viruses MVAlucgpt, MVA A675, or with V+ATIs produced by and containing MVA-ATI, MVA-ATI-2, or a combination of the binary vaccine vectors MVA (p4c,delta ATI) and MVA(delta p4c,ATI) on day) only, using $1 \times 10^5$, $1 \times 10^6$ or $1 \times 10^7$ PFU (Peacock et al, J. Virol. 78(23): 13163-13172 (2004)). The infectious titer of MVA-ATI can be determined after releasing the IMV from ATIs dissolved in buffer at high pH (Ichihashi and Matsumoto, Virology 29:264-275 (1966)). Serum and salivary secretions can be collected on days 14 and 35 and tested for the presence of IgG and IgA antibodies using purified MVA virus and the CPXV protein B5R as ELISA coating antigens. The CPXV B5R protein can be used, this protein is 94% identical to that of the MVA protein. Serum vaccinia virus-neutralizing antibodies can also be evaluated using a plaque reduction assay. On day 35, spleen and lung mononuclear cells can be isolated and tested for the presence of antigen-specific IFN-γ secreting cells by ELISPOT. An evaluation can be made of CD8-mediated cellular responses against the recently identified (Tscharke et al, J. Exp. Med. 201(11):95-104 (2005)) H-2Kb-restricted CTL epitopes in vaccinia B8R (TSYKFESV; also a CTL epitope in MVA) and A19L (VSLDYINTM; also a CTL epitope in MVA) using an IFN-γ ELISPOT assay (Peacock et al, J. Virol. 78(23):13163-13172 (2004), Staats et al, J. Immunol. 167:5386-5394 (2001)). The magnitude of antigen-specific humoral and cell mediated immune responses induced by the various MVA (lacking-ATIs) and MVA viruses embedded in ATIs can be compared statistically using ANOVA and comparison of multiple means procedures using S-Plus software (Peacock et al, J. Virol. 78(23):13163-13172 (2004)).

Previous studies have demonstrated that ID immunization with $1 \times 10^7$ recombinant MVA induced maximal antigen-specific CD8 IFN-γ and tetramer responses (Peacock et al, J. Virol. 78(23):13163-13172 (2004)), however, antigen-specific antibody responses were not evaluated. Others have recently reported that intramuscular inoculation of MVA to macaques at day 0 and at eight weeks induced B5R- and whole virus-specific serum IgG and cowpox virus-neutralizing antibodies comparable to that induced by a single Dryvax inoculation given at the time of the MVA boost (Earl et al, Nature 428(6979):182-5 (2004)). The use of $1 \times 10^5$, $1 \times 10^6$ and $1 \times 10^7$ PFU of MVA and the IN, intramuscular, gastric (e.g., oral) and ID routes can allow identification of the route of inoculation and the dose of MVA required for induction of maximum humoral and cell-mediated responses. Detection of antigen-specific IgA in only salivary secretions of mice inoculated by the IN or gastric routes is expected since only mucosal immunization induces optimal antigen-specific IgA in mucosal secretions (Bradney et al, Journal of Virology 76(2):517-524 (2002), Staats et al, J. Immunol. 157(1):462-72 (1996)). Similar methodologies can be applied to measure the efficacies of the various MVA vaccines to induce humoral and cellular immune responses to other antigens (such as influenza virus proteins) expressed by the vaccine vectors.

Inoculation of mice with the MVA-ATI virus can result in the induction of MVA-specific humoral and cell-mediated immune responses that are significantly greater than those induced after inoculation of mice with MVAlucgpt virus or other control MVA viruses. Establishment of this model permits determination if the modifications made to MVA result in the induction of significantly increased antigen-specific humoral and/or cell-mediated immune responses. It can be determined if the increased immunogenicity provides significantly better protection against illness after vaccinia virus challenge than the unmodified MVA vaccine virus.

EXAMPLE 5

ATI preparations can be made according to a procedure modified from that described by Patel et al (Virology 149, 174-189 (1986)). A monolayer of permissive cells (about $10^8$ cells per bottle) in a roller bottle (850 cm) can be infected with 10 pfu/cell of virus (rotating the culture at 37 degrees for 45 min). After infection, 100 ml of 5% fetal bovine serum/MEME, can be added and the culture incubated for 36 hrs. The cells can be suspended in the culture fluid by shaking. Then the cells can be collected by centrifugation at 10,000 rpm for 15 min in Sorvall GSA rotor at 4° C., keeping everything at 4° C. for rest of protocol. The pelleted cells can be resuspended in 10 ml of phosphate-buffered saline (PBS)/5 mM EDTA/1× protease inhibitor tab (Roche #11836170). This material can be homogenized by 100 strokes in a tight-fitting Dounce homogenizer, and checked for lysed nuclei by microscopy. If nuclei are not lysed, then the material can be passed 10 times (or as many times as needed) through a 10-ml syringe with 22 G needle. The volume can be brought to 200 ml in EPBS (PBS containing 5 mM EDTA and 1 mM PMSF). ATIs can be collected by centrifugation at 600 g for 15 min. The pellet containing the ATIs can be washed with 200 ml EPBS. The pellet of ATIs can be resuspended in 5 ml EPBS containing protease inhibitors by sonicating in a water bath sonicator. Alternatively, the ATI pellet can be resuspended in 5 ml of 0.5 M sodium bicarbonate (pH 11) to solubilize the ATIs.

All documents and other information sources cited above are hereby incorporated in their entirety by reference.

What is claimed is:

1. A recombinant modified vaccinia Ankara (MVA) virus comprising an ati gene and a p4c gene wherein, upon introduction of said recombinant MVA virus into a permissive host cell, A-type inclusions are produced comprising intracellular mature virus.

2. The recombinant MVA virus according to claim 1 wherein said ati gene is a cowpox virus ati gene.

3. The recombinant MVA virus according to claim 1 wherein said p4c gene is a vaccinia virus p4c gene.

4. The recombinant MVA virus according to claim 1 wherein said recombinant MVA virus further comprises a marker gene.

5. The recombinant MVA virus according to claim 1 wherein said p4c gene and ati gene are substituted for disrupted p4c and ati genes, respectively, of MVA.

6. The recombinant MVA virus according to claim 1 wherein said recombinant MVA virus further comprises a sequence encoding at least one non-poxvirus immunogen.

7. The recombinant MVA virus according to claim 6 wherein said at least one immunogen is at least one influenza virus immunogen.

8. The recombinant MVA virus according to claim 7 wherein said at least one influenza virus immunogen comprises influenza virus hemagglutinin (HA).

9. An isolated A-type inclusion comprising the recombinant MVA virus according to claim 1.

10. A composition comprising the A-type inclusion according to claim 9, and a carrier.

11. A composition comprising recombinant vaccinia viruses that, upon introduction into permissive host cells, embed intracellular mature viruses (IMVs) within A-type inclusions, wherein said recombinant vaccinia viruses comprise a sequence encoding at least one non-poxvirus immunogen.

12. A composition comprising recombinant vaccinia viruses that, upon introduction into permissive host cells, embed intracellular mature viruses (IMVs) within A-type inclusions, wherein said composition comprises a first population of recombinant MVA viruses comprising an ati gene and a second, different population of recombinant MVA viruses comprising a p4c gene.

13. The composition according to claim 12 wherein said composition further comprises a third, different population of recombinant MVA viruses comprising a sequence encoding at least one non-poxvirus immunogen.

14. An isolated A-type inclusion comprising an MVA virus.

15. The A-type inclusion according to claim 14 wherein said A-type inclusion comprises: (i) a recombinant MVA virus comprising an ati gene, or (ii) a recombinant MVA virus comprising a p4c gene, or both (i) and (ii).

16. The A-type inclusion according to claim 15 wherein said A-type inclusion comprises both (i) and (ii).

17. A composition comprising the A-type inclusion according to claim 14 and a carrier.

18. A composition comprising: (i) A-type inclusions comprising at least a recombinant MVA virus comprising an ati gene and (ii) A-type inclusions comprising at least a recombinant MVA virus comprising a p4c gene, and a carrier.

19. A method of inducing an immune response in a patient comprising administering to said patient an amount of said A-type inclusion according to claim 9 or 14 or an amount of said composition according to claim 18, sufficient to induce said response.

20. The method according to claim 19 wherein said response is an anti-poxvirus response.

21. The method according to claim 19 wherein said immune response is against a non-poxvirus immunogen.

22. The method according to claim 19 wherein said patient is a human.

23. The method according to claim 19 wherein said administration is effected intranasally, intramuscularly, orally, or intradermally.

24. The method according to claim 23 wherein said administration is effected intradermally with microneedles.

* * * * *